United States Patent [19]

Naito et al.

[11] Patent Number: 5,162,522

[45] Date of Patent: Nov. 10, 1992

[54] METHOD FOR PRODUCING CEPHEM COMPOUNDS

[75] Inventors: Kenzo Naito, Kyoto; Yukio Ishibashi, Toyonaka; Toshihiko Fujitani, Tsukuba, all of Japan

[73] Assignee: Takeda Chemical Industries, Ltd., Osaka, Japan

[21] Appl. No.: 691,307

[22] Filed: Apr. 25, 1991

Related U.S. Application Data

[63] Continuation of Ser. No. 391,170, Aug. 9, 1989, abandoned.

[30] Foreign Application Priority Data

Aug. 10, 1988 [JP] Japan .................. 63-200910

[51] Int. Cl.$^5$ .......................................... C07D 501/04
[52] U.S. Cl. ................................. 540/230; 540/222; 540/215; 540/221
[58] Field of Search ............. 540/230, 222, 221, 215, 540/227

[56] References Cited

U.S. PATENT DOCUMENTS 4,323,676  4/1982  Tsushima et al. .................. 544/22
4,584,371  4/1986  Timko .................................. 544/16
4,908,444  3/1990  Naito et al. ........................ 540/230

FOREIGN PATENT DOCUMENTS 1544103  4/1979  United Kingdom .

OTHER PUBLICATIONS

J. Org. Chem., 1984, vol. 49, No. 4, pp. 722–725.
R. J. Clemens, "Diketene," Chemical Reviews, vol. 86, No. 2, Apr. 1986, pp. 247–253, American Chemical Society, Washington, D.C., USA.

*Primary Examiner*—Nicholas S. Rizzo
*Attorney, Agent, or Firm*—Wegner, Cantor, Mueller & Player

[57] ABSTRACT

A method for producing 3-(3-oxobutyryloxymethyl)-3-cepham-4-carboxylic acids which are antibiotics or intermediates for the synthesis of antibiotics, at a low temperature in a very short period of time and in good yield, characterized by reacting a 3-hydroxylmethyl-3-cephem-4-carboxylic acid with diketene in the presence of a 4-(tertiary-amino)pyridine and if necessary, when a 7-acylamino-3-(3-oxobutyryloxymethyl)-3-cephem-4-carboxylic acid is obtained, subjecting it to deacylation at the 7-position thereof.

20 Claims, No Drawings

METHOD FOR PRODUCING CEPHEM COMPOUNDS

This application is a continuation application of U.S. Ser. No. 07/391,170 filed Aug. 9, 1989, now abandoned.

This invention relates to an industrially advantageous method of producing 3-(3-oxobutyryloxymethyl)-3-cephem-4-carboxylic acids (hereinafter referred to as "3-butyryl compounds"), which are antibiotics or intermediates for the synthesis of antibiotics, using the corresponding 3-hydroxymethyl-3-cephem-4-carboxylic acids (hereinafter referred to as "3-hydroxy compounds").

The 3-butyryl compounds are of importance as antibacterial compounds or as intermediates for the synthesis of anti-bacterial compounds and how to produce them has been the subject of a number of investigations.

The use of the 3-butyryl compounds as intermediates is described, for example, in Chemical Reviews, 86, 251–252 (1986); and U.K. Patent No. 1 544 103.

A method known for the production of the 3-butyryl compounds comprises reacting the 3-hydroxy compounds with diketene and such a production method is described, for example, in Chemical Reviews, 86, 251–252 (1986); and U.K. Patent No. 1 544 103.

Those 3-butyryl compounds which have an acylamino group at the 7-position thereof can be converted to the corresponding 7-amino-3-(3-oxobutyryloxymethyl)-3-cephem-4-carboxylic- acids (hereinafter referred to as "7-amino-3-butyryl compounds") by deacylation at position 7. Such a method of production is described, for example, in U.K. Patent No. 1 544 103.

However, the above-mentioned prior art method of synthesizing the 3-butyryl compounds cannot be said to be always advantageous from the commercial production viewpoint. Thus, for example, said method is disadvantageous in that a reaction period of at least 30 minutes is generally required for the reaction to be complete, that the reaction hardly proceeds at low temperatures and that the yields of the desired products are not always high.

In particular, when the synthesis of the 3-butyryl compounds having an acylamino group at position 7 is to be followed by deacylation at position 7, the synthesis of the 3-butyryl compounds should efficiently- be carried out at low temperatures since the deacylation at position 7 is carried out at low temperatures. However, the prior art method of synthesizing the 3-butyryl compounds, when carried out at low temperatures, requires a long reaction period, hence cannot be said to be advantageous from the commercial viewpoint.

The present inventors made various investigations in an attempt to develop a commercially advantageous method of producing the 3-butyryl compounds and, as a result, found that when the 3-hydroxy compounds are reacted with diketene in the presence of a 4-(tertiary-amino)pyridine, the reaction unexpectedly reaches completion in a very short period of time as compared with the prior art method to give the desired 3-butyryl compounds in better yields, the reaction progresses advantageously even at low temperatures and the resulting 3-butyryl compounds, if they have an acylamino group at position 7, can be subjected in the reaction mixture form without isolation or purification to deacylation at position 7 in the same reactor and under the same low temperature conditions to give the 7-amino-3-butyryl compounds with good efficiency. The present invention has been completed based on these findings.

Thus the invention is directed to:

(1) a method of producing the 3-butyryl compounds which comprises reacting the 3-hydroxy compounds with diketene in the presence of a 4-(tertiary-amino)-pyridine and (2) a method of producing the 7-amino-3-butyryl compounds which comprises reacting 7-acylamino-3-hydroxymethyl-3-cephem-4-carboxylic acids (hereinafter referred to as "7-acylamino-3-hydroxy compounds") with diketene in the presence of a 4-(tertiary-amino)pyridine and subjecting the resulting 7-acylamino-3-(3-oxobutyryloxymethyl)-3-cephem-4-carboxylic acids (hereinafter referred to as "7-acylamino-3-butyryl compounds") to deacylation at position 7.

The 3-hydroxy compounds which are to be used as the starting materials in the practice of the invention are 3-cephem compounds having a hydroxymethyl group at position 3 and a carboxyl group at position 4, or salts or esters thereof. Thus, for example, those 3-hydroxy compounds that are obtainable by fermentative production or derivable from the fermentation products by chemical or enzymatic treatment are used as the starting materials in the practice of the invention. Preferred examples of such 3-hydroxy compounds are compounds of the formula

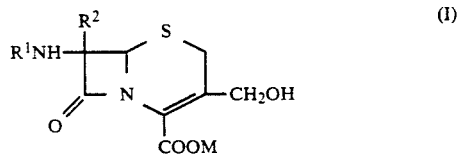

wherein $R^1$ is a hydrogen atom, a protective group or an acyl group, $R^2$ is a hydrogen atom or a methoxy or formylamino group and M is a hydrogen atom, a salt-forming group or an ester residue.

The 7-acylamino-3-hydroxy compounds to be used are 3-cephem compounds having an acylamino group at position 7, a hydroxymethyl group at position 3 and a carboxyl group at position 4, or salts or esters thereof, for example those 3-hydroxy compounds which have an acylamino group at position 7. Preferred examples of such 7-acylamino-3-hydroxy compounds are compounds of the formula

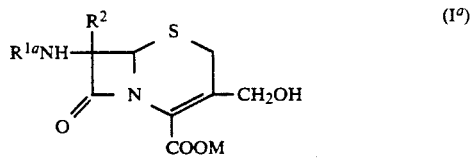

wherein $R^{1a}$ is an acyl group and other symbols are as defined above.

Particularly preferred examples of the compounds (I) or ($I^a$) are amphoteric substances insoluble in anhydrous organic solvents, for example compounds of the formula

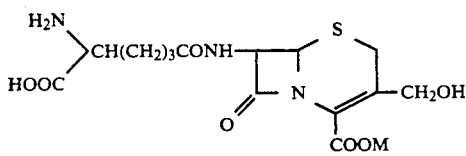

wherein M is as defined above. A typical example of such amphoteric substances (I$^b$) is desacetylcephalosporin C, which is produced at high unit levels by fermentation processes or is a by-product in the fermentative production of cephalosporin C.

The 3-butyryl compounds obtainable according to the invention are 3-cephem compounds having an 3-oxobutyryl oxymethyl group at position 3 and a carboxyl group at position 4, or salts or esters thereof. Preferred examples of the 3-butyryl compounds are compounds of the formula

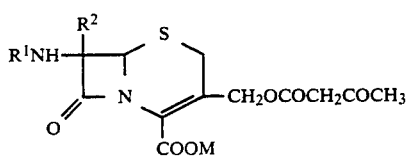

wherein the symbols are as defined above, which are obtainable by reacting the compounds (I) with diketene in the presence of a 4-(tertiary-amino)pyridine.

The 7-acylamino-3-butyryl compounds are 3-cephem compounds having an acylamino group at position 7, an 3-oxobutyryloxymethyl group at position 3 and a carboxyl group at position 4, or salts or esters thereof and correspond to those 3-butyryl compounds having an acylamino group at position 7. Preferred examples of the 7-acylamino-3-butyryl compounds are compounds of the formula

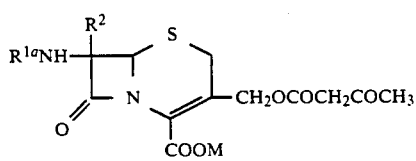

wherein the symbols are as defined above, which are obtainable by reacting the compounds (I$^a$) with diketene in the presence of a 4-(tertiary-amino)pyridine.

Particularly preferred examples of the compounds (II) or (II$^a$) are compounds of the formula

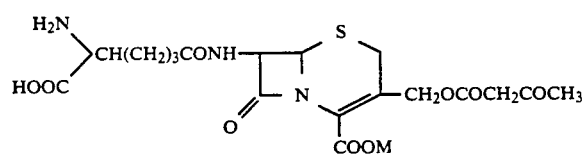

wherein M is as defined above, which are obtainable by using the compounds (I$^b$) as the starting materials.

The 7-amino-3-butyryl compounds are 3-cephem compounds having an amino group at position 7, an 3-oxobutyryloxymethyl group at position 3 and a carboxyl group at position 4, or salts or esters thereof and correspond to the 3-butyryl compounds having an amino group at position 7. Preferred examples of the 7-amino-3-butyryl compounds are compounds of the formula

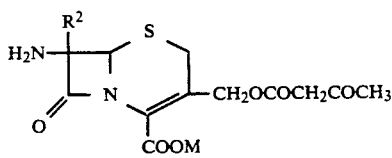

wherein R$^2$ and M are as defined above, which are obtainable by subjecting the compounds (II$^a$) to deacylation at position 7, and most preferred examples of them include the compounds (II$^c$) where R$^2$=H, i.e. of the formula:

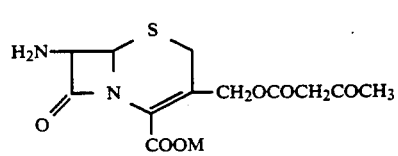

wherein M is as defined above, which are obtainable by subjecting the compounds (II$^b$) to deacylation at position 7.

The acyl group represented by R$^1$ in the above formula (I) or (II) and the acyl group represented by R$^{1a}$ in the formula (I$^a$) or (II$^a$) each includes phenylacetyl, phenoxyacetyl and 5-amino-5-carboxyvaleryl groups whose amino or carboxyl group may optionally be protected and further includes other substituents at position 6 or 7 of various penicillin or cephalosporin derivatives, for example aliphatic carboxylic acid acyl groups, such as formyl, acetyl, propionyl, hexanoyl, butanoyl, heptanoyl, octanoyl and cyclopentanoyl (cyclopentylcarbonyl), substituted aliphatic carboxylic acid acyl groups whose amino and/or carboxyl group may optionally be protected, such as 2-thienylacetyl, tetrazolylthioacetyl, tetrazolylacetyl, cyanoacetyl, acetoacetyl, 4-methylthio-3-oxobutyryl, 4-carbamoylmethylthio-3-oxobutyryl, α-phenoxypropionyl, α-phenoxybutyryl, p-nitrophenylacetyl, (2-pyridyloxy)acetyl, (3-pyridyloxy)acetyl, (4-pyridyloxy)acetyl, (2-oxothiazolin-4-yl)acetyl, (2-aminothiazol-4-yl)acetyl, 4-pyridylthioacetyl, (3-sydnone)acetyl, 1-pyrazolylacetyl, 2-furylacetyl, (2-oxo-3-methylpyridazin-6-yl)thioacetyl, α-carboxyphenylacetyl, α-aminophenylacetyl, mandelyl, α-sulfophenylacetyl, α-sulfo-(p-aminopenyl)acetyl, phenylglycyl, 1-cyclohexenylglycyl, thienylglycyl, furylglycyl, cyclohexadienylglycyl, α-(β-methylsulfonylethoxycarbonyl)aminophenylacetyl, 2-(2-amino-4-thiazolyl)-2-methoxyiminoacetyl, 2-(2-amino-4-thiazolyl)-2-[(1-methyl-1-carboxyethyl)oxyimino]acetyl and 2-(2-amino-4-thiazolyl)-2-carboxymethoxyiminoacetyl, aromatic acyl groups, such as benzoyl and p-nitrobenzoyl, and heterocyclic acyl groups, such as 5-methyl-3-phenyl-4-isoxazolylcarbonyl and 3-(2,6-dichlorophenyl)-5-methyl-4-isoxazolylcarbonyl.

The functional groups in the above-mentioned compounds, for example the 7-position amino group in formula (I) or (II) [in cases where, in formula (I) or (II), $R^1=H$] or the amino and/or carboxyl group in the 7-position acyl group in formula (I), (I$^a$), (I$^b$), (II), (II$^a$) or (II$^b$), may be suitably protected. Thus, for example, the following groups may be used as the amino-protecting group [inclusive of the protective group represented by $R^1$ in formula (I) or (II)]: aromatic acyl groups, such as phthaloyl, benzoyl, p-nitrobenzoyl, toluoyl, naphthoyl, p-tert-butylbenzoyl, p-tert-butylbenzenesulfonyl, phenylacetyl, benzenesulfonyl, phenoxyacetyl, toluenesulfonyl and chlorobenzoyl, aliphatic acyl groups, such as acetyl, valeryl, caprylyl, n-decanoyl, acryloyl, pivaloyl, camphorsulfonyl, methanesulfonyl and chloroacetyl, esterified carboxyl groups, such as ethoxycarbonyl, isobornyloxycarbonyl, phenoxycarbonyl, trichloroethoxycarbonyl and benzyloxycarbonyl, and substituted carbamoyl or thiocarbamoyl groups, such as methylcarbamoyl, phenylcarbamoyl, naphthylcarbamoyl, phenylthiocarbamoyl and naphthylthiocarbamoyl. The carboxyl-protecting group may be selected from among those generally used in the field of $\beta$-lactam and peptide chemistry, such as, for example, benzyl, p-nitrobenzyl, t-butyl, trityl, trimethylsilyl, dimethylchlorosilyl and 2-trimethylsilylethyl.

Referring to the formulas (I), (I$^a$), (II), (II$^a$) and (IIc) shown above, $R^2$ is, for example, a hydrogen atom or a methoxy or formylamino group. As the salt-forming group represented by M in formulas (I), (I$^a$), (I$^b$), (II), (II$^a$), (II$^b$), (II$^c$) or (II$^d$) frequent use is made of alkali metals, such as lithium, sodium and potassium, alkaline earth metals, such as magnesium and calcium, and ammonium groups derived from various amines and the like such as dicyclohexylamine, triethylamine, tributylamine, diethylamine and trimethylamine, while, as the ester residue represented by M use is made of $C_{1-6}$ alkyl groups (e.g. methyl, ethyl, n-propyl, isopropyl, tert-butyl, tert-amyl), aralkyl groups [e.g. benzyl, p-nitrobenzyl, p-methoxybenzyl, diphenylmethyl, bis(p-methoxyphenyl)methyl], substituted-oxymethyl groups (e.g. $C_{1-4}$ alkoxymethyl, such as methoxymethyl or ethoxymethyl, $C_{7-10}$ aralkyloxymethyl, such as benzyloxymethyl, $C_{2-5}$ acyloxymethyl, such as acetoxymethyl or pivaloyloxymethyl), silyl groups (e.g. trimethylsilyl, tert-butyldimethylsilyl, dimethylchlorosilyl), and aryl groups (e.g. phenyl, naphthyl), among others.

The 4-(tertiary-amino)pyridine to be used is a pyridine substituted by a tertiary amino group at the 4-position thereof. As such pyridine, there may be mentioned, for example, compounds of the formula

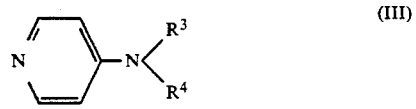

(III)

wherein $R^3$ and $R^4$ are the same or different and each is an alkyl group, or $R^3$ and $R^4$, together with the adjacent nitrogen atom, represent a cyclic amino group. The alkyl group represented by each of $R^3$ and $R^4$ in formula (III) is, for example, a lower alkyl group containing 1 to 6 carbon atoms, such as methyl, ethyl, propyl, isopropyl or butyl. As the cyclic amino group represented by $R^3$ and $R^4$ together with the adjacent nitrogen atom, there may be mentioned, for example, piperidino, 4-methylpiperidino or pyrrolidino. Specific examples of the pyridine (III) are 4-(dimethylamino)pyridine, 4-(diethylamino)pyridine, 4-(di-n-propylamino)pyridine, 4-(diisopropylamino)pyridine, 4-(N-methyl-N-ethylamino)pyridine, 4-(N-ethyl-N-propylamino)pyridine, 4-pyrrolidinopyridine, 4-(4-methylpyrrolidino)pyridine and 4-piperidinopyridine, among others. These 4-(tertiary-amino)pyridines can be recovered after the reaction and the recovered ones can be reused.

Preferred 4-(tertiary-amino)pyridines are 4-(di-$C_{1-3}$ alkylamino)pyridines, such as 4-(dimethylamino)pyridine.

The method according to the invention can be carried out by reacting the 3-hydroxy compounds with diketene in the presence of the 4-(tertiary-amino)pyridine.

Generally, this reaction is carried out in a solvent. Any solvent may be used as such solvent provided that it will not interfere with the reaction. Thus, for example, use may be made of halogenated hydrocarbons, such as methylene chloride, chloroform and dichloroethane, amides, such as N,N-dimethylformamide and N,N-dimethylacetamide, ethers, such as tetrahydrofuran and dioxane, nitriles, such as acetonitrile, esters, such as ethyl acetate, and mixtures of these. Halogenated hydrocarbons, such as methylene chloride, are preferred among others. These solvents are used generally in an amount of 0.05 to 50 liters, preferably 0.5 to 25 liters, per mole of 3-hydroxy compounds. Since the reaction proceeds stoichiometrically, it is enough to use diketene in an equimolar amount relative to the 3-hydroxy compounds. It is possible, however, to use diketene in excess (for example, 1 to 1.5 moles per mole of 3-hydroxy compounds) so that the loss thereof due to decomposition, which may occur in the presence of water or an alcohol, can be recovered. In cases where the 3-hydroxy compounds have a free amino group at position 7, said amino group is also acetoacetylated by excess diketene. The present invention includes such cases within the scope thereof as well. The 4-(tertiary-amino)pyridine can promote the reaction in a catalytic amount and is used generally in an amount of 0.001 to 1 mole, preferably 0.001 to 0.02 mole, per mole of diketene. The reaction temperature to be used is generally within the range of $-40°$ to $40°$ C., preferably $-20°$ to $25°$ C., more preferably $-10°$ to $5°$ C., and thus the reaction can be carried out at lower temperatures than in cases where no 4-(tertiary-amino)pyridine is used. While the reaction period required may vary to some extent depending on the reaction temperature, the reaction generally reaches completion in a very short period (less than 30 minutes, preferably 1 to 20 minutes). When the reaction temperature is low, the time required for the reaction to reach completion may be one tenth or less as compared with the prior art methods which do not use any 4-(tertiary-amino)pyridine. For instance, when the reaction is carried out at about $0°$ C. ($-5°$ to $0°$ C.), the reaction can reach completion generally in 10 to 20 minutes.

The thus-produced 3-butyryl compounds can be isolated and purified by per se known means, for example concentration, concentration under reduced pressure, solvent extraction, pH adjustment, solvent exchange, crystallization, recrystallization, chromatography, etc. When they are to serve as intermediates, they may be submitted to the next step in the reaction mixture form without isolation.

In a further aspect, the method according to the invention comprises reacting the 7-acylamino-3-hydroxy compounds with diketene in the presence of the 4-(tertiary-amino)pyridine and then subjecting the resulting 7-acylamino-3-butyryl compounds to deacylation at position 7.

The reaction of the 7-acylamino-3-hydroxy compounds with diketene in the presence of the 4-(tertiary-amino)pyridine can be carried out in the same manner as the above-mentioned reaction of the 3-hydroxy compounds with diketene in the presence of the 4-(tertiary-amino)pyridine. The thus-obtained 7-acylamino-3-butyryl compounds can be subjected, in the reaction mixture form, to deacylation at position 7 to give the corresponding 7-amino-3-butyryl compounds. The deacylation at position 7 can be performed by a per se known method [for example, the method described in U.S. Pat. No. 3,697,515, U.S. Pat. No. 3,499,909, U.S. Pat. No. 3,882,108 or U.S. Pat. No. 3,632,578]. In carrying out this reaction, the presence of the 4-(tertiary-amino)pyridine in the reaction mixtures will not produce any particular adverse effect and, therefore, it is not necessary to eliminate the 4-(tertiary-amino)pyridine from the reaction mixtures. Thus, for example, the 7-acylamino-3-butyryl compounds each in the form of a reaction mixture, if necessary after protection of the carboxyl group by a conventional method (preferably with trimethylsilyl, dimethylchlorosilyl, propionyl, acetyl, etc.), can be converted to the corresponding imino halides by reaction with an imino halide-forming agent (e.g. phosphorus pentachloride). The latter reaction is preferably carried out in the presence of a tertiary amine, such as N,N-dimethylaniline or N,N-diethylaniline. The reaction temperature is not particularly critical but should preferably be within the range of $-55°$ C. to $0°$ C. The thus-produced imino halides are then converted to the corresponding imino ethers by addition to the imino halides of a lower alcohol, such as methanol, ethanol, n-propanol, n-butanol or isobutanol. The thus-produced imino ethers are subjected to solvolysis with water, a lower alcohol or the like. Upon adjustment of the pH of the reaction mixtures approximately to the respective isoelectric points of the 7-amino-3-butyryl compounds, the 7-amino-3-butyryl compounds precipitate out. The precipitates are collected by filtration, washed with an organic solvent, such as acetone or dichloromethane, and dried to give the 7-amino-3-butyryl compounds.

The thus-obtained 3-butyryl compounds and 7-amino--3-butyryl compounds may be converted as necessary to appropriate salts or esters (inclusive of pharmacologically acceptable salts or esters) by a conventional method when they are in the free form (M=H), or to their free form by a conventional method when they are in the form of salts or esters (M=salt-forming group or ester residue). They are used as antibacterial substances in the free form or in the form of such salts or esters as mentioned above or, further, in the form of other appropriate salts or esters derived therefrom. They are useful as starting materials for the production of more potent antibacterial substances as well.

The 3-hydroxy compounds to be used as the starting materials in the practice of the invention can be produced, for example, by a fermentative method [e.g. the method described in Nature, 246, 154 (1973) or in U. S. Pat. No. 3,926,729] or by chemical or enzymatic treatment of such fermentation products [e.g. by the method described in Biochemical Journal, 81, 591–596 (1961)].

The desired 3-butyryl compounds as such may be used as antibiotics having good antibacterial activity in the conventional manner [e.g. by the method described in U.S. Pat. No. 4,098,888]. They may be used also as intermediates for the synthesis of antibiotics having better antibacterial activity. For instance, the 3-butyryl compounds can be converted to the corresponding 7-[2-(2-imino-4-thiazolin-4-yl)acetamido] compounds [described, for example, in U.S. Pat. No. 4,080,498] by subjecting the former to 7-position acyl group elimination by a per se known method [e.g. the method described in U.S. Pat. No. 3,697,515, U.S. Pat. No. 3,499,909, U.S. Pat. No. 3,882,108 or U.S. Pat. No. 3,632,578], followed by reaction with a 4-halo-3-oxobutyryl halide, and then reacting the resultant 4-halo-3-oxybutyrylamido compounds with thiourea. The 7-[2-(2-imino-4-thiazolin-4-yl)acetamido] compounds can be further reacted with a nucleophilic compound with ease by a per se known method [e.g. the method described in U.K. Patent No. 1 544 103 or EP-160252A] to give compounds having the residue of said nucleophilic compound as introduced into the 3-position methyl group. In either case, the final products have good antibacterial activity.

The following examples are further illustrative of the present invention but are by no means limitative of the scope thereof.

In the working examples and reference examples, the symbols used have the following meanings:

g: gram(s); mg: milligram(s); ml: milliliter(s); s: singlet; br: broad; d: doublet; dd: double doublet; ABq: AB type quartet; m: multiplet; $CF_3COOD$: deuterated trifluoroacetic acid; $DMSO-d_6$: dimethyl sulfoxide-$d_6$; the NMR (nuclear magnetic resonance spectrum) data given are chemical shift values expressed in terms of $\delta$ values (ppm) as measured at 90 MHz with tetramethylsilane as an internal standard.

EXAMPLE 1

To a solution of 6.96 g of 7β-(D-5-carboxy-5-phenoxycarbonylaminovaleramido)-3-hydroxymethyl-3-cephem-4-carboxylic acid ditriethylamine salt and 50 mg of 4-(dimethylamino)pyridine in 50 ml of methylene chloride was added 0.92 g of diketene at 0° C., and the mixture was stirred at that temperature for 15 minutes. After completion of the reaction, the solvent was distilled off under reduced pressure, 50 ml of water added to the residue, and the resultant solution adjusted to pH 1.5 by addition of concentrated hydrochloric acid and then extracted with two 50-ml portions of a methylene chloride-tetrahydrofuran mixture (2:1 by volume). The organic layers were combined and concentrated to dryness. The residue was dissolved in aqueous acetonitrile (30 ml of acetonitrile plus 15 ml of water), the solution adjusted to pH 6.5 by addition of 2N aqueous sodium hydroxide, the organic solvent distilled off under reduced pressure, and the residue lyophilized to give 6.05 g of 7β-(D-5-carboxy-5-phenoxycarbonylaminovaleramido)-3-(3-oxobutyryloxymethyl)-3-cephem-4-carboxylic acid disodium salt. Yield 97.3%.

NMR (DMSO-$d_6$): δ 1.4–1.8 (4H, m), 2.08 (3H, s), 2.0–2.3 (2H, m), 3.17 & 3.47 (2H, ABq, J=17 Hz), 3.38 (2H, br.s), 3.5–3.8 (1H, m), 4.86 & 5.09 (2H, ABq, J=12 Hz), 4.92 (1H, d, J=5 Hz), 5.48 (1H, dd, J=5 & 8 Hz), 6.7–7.5 (5H, m), 6.86 (1H, d, J=8 Hz), 8.60 (1H, d, J=8 Hz) ppm IR (KBr): 1740, 1606 cm$^{-1}$

EXAMPLE 2

To a solution of 6.96 g of 7β-(D-5-carboxy-5-phenoxycarbonylaminovaleramido)-3-hydroxymethyl-3-cephem-4-carboxylic acid ditriethylamine salt and 50 mg of 4-(dimethylamino)pyridine in 80 ml of methylene chloride was added 0.92 g of diketene at 0° C., and the mixture was stirred at that temperature for 15 minutes. After completion of the reaction, 10.9 g of N,N-dimethylaniline and 3.10 g of dimethyldichlorosilane were added to the reaction mixture. The resultant mixture was stirred at the same temperature for 20 minutes and then cooled to −40° C. At that temperature, 5.62 g of phosphorus pentachloride was added and the mixture stirred for 30 minutes. This reaction mixture was added dropwise to 40 ml of methanol at 0° C. over 10 minutes. The resultant mixture was stirred at that temperature for 10 minutes, 50 ml of water added, and the mixture stirred for 5 minutes. After phase separation, 50 ml of methanol was added to the aqueous layer, and the solution adjusted to pH 3.5 by dropwise addition of 10% aqueous sodium hydroxide. The precipitated crystalline powder was collected by filtration, washed in sequence with 20 ml of water and 20 ml of acetone and dried under reduced pressure to give 2.85 g of 7β-amino-3-(3-oxobutyryloxymethyl)-3-cephem-4-carboxylic acid. Yield 90.7%.

NMR (CF$_3$COOD): δ 2.47 (3H, s), 3.78 (2H, s), 3.61 & 3.86 (2H, ABq, J=18 Hz), 5.27 & 5.54 (2H, ABq, J=13 Hz), 5.47 & 5.92 (each 1H, d, J=4.6 Hz) ppm IR (KBr): 1798, 1620 cm$^{-1}$

EXAMPLE 3

The procedure of Example 1 was repeated except that 50 mg of 4-pyrrolidinopyridine was used in lieu of 50 mg of 4-(dimethylamino)pyridine. The procedure yielded 6.06 g of 7β-(D-5-carboxy-5-phenoxycarbonylaminovaleramido)-3-(3-oxobutyryloxymethyl)-3-cephem-4 carboxylic acid disodium salt. Yield 97.5%

The NMR spectrum and IR spectrum of this product were in good agreement with those of the compound obtained in Example 1.

EXAMPLE 4

To a solution of 6.48 g of 7β-(D-5-carboxy-5-ethoxycarbonylaminovaleramido)-3-hydroxymethyl-3-cephem-4-carboxylic acid ditriethylamine salt and 50 mg of 4-(dimethylamino)pyridine in 50 ml of methylene chloride was added 0.92 g of diketene at 0° C., and the mixture was stirred at that temperature for 15 minutes. After completion of the reaction, the solvent was distilled off under reduced pressure, 50 ml of water added to the residue, and the resultant solution adjusted to pH 1.5 by addition of concentrated hydrochloric acid and then extracted with two 50-ml portions of a methylene chloride-tetrahydrofuran mixture (2:1 by volume). The organic layers were combined and concentrated to dryness. The residue was dissolved in aqueous acetonitrile (30 ml of acetonitrile plus 15 ml of water), the solution adjusted to pH 6.5 by addition of 2N aqueous sodium hydroxide, the organic solvent distilled off under reduced pressure, and the residue lyophilized to give 5.50 g of 7β-(D-5-carboxy-5-ethoxycarbonylaminovaleramido)-3-(3-oxobutyryloxymethyl)-3-cephem-4-carboxylic acid disodium salt. Yield 95.9%

NMR(DMSO-d$_6$): δ 1.15 (3H,t,J=7H$_2$), 1.3-1.8 (4H,m), 2.16 (3H,s), 2.0-2.3 (2H,m), 3.17 and 3.67 (2H,ABq,J=17 Hz), 3.58 (2H,s), 3.95 (2H,q,J=7 Hz), 4.86 and 5.09 (2H,ABq,J=12 Hz), 4.92 (1H,d,J=5 Hz), 5.48 (1H,dd,J=5×8 Hz), 6.26 (1H,d,J=7 Hz), 8.63 (1H,d,J=8 Hz) ppm IR(KBr): 1764, 1604 cm$^{-1}$

EXAMPLE 5

To a solution of 7.06 g of 7β-(D-5-carboxy-5-phthalimidovaleramido)-3-hydroxymethyl-3-cephem-4-carboxylic acid ditriethylamine salt and 50 mg of 4-(dimethylamino)pyridine in 50 ml of methylene chloride was added 0.92 g of diketene at 0° C., and the mixture was stirred at that temperature for 15 minutes. After completion of the reaction, the solvent was distilled off under reduced pressure, 50 ml of water added to the residue, and the resultant solution adjusted to pH 1.5 by addition of concentrated hydrochloric acid and then extracted with two 50-ml portions of a methylene chloride-tetrahydrofuran mixture (2:1 by volume). The organic layers were combined, dried over anhydrous magnesium sulfate, and concentrated to dryness under reduced pressure.

To the residue was added 50 ml of ethyl ether, and the precipitated powder was collected by filtration, washed with 50 ml of ethyl ether and dried under reduced pressure to give 5.66 g of 7β-(D-5-carboxy-5-phthalimidovaleramido)-3-(3-oxobutyryloxymethyl)-3-cephem-4-carboxylic acid. Yield 96.3%

NMR(DMSO-d$_6$): δ1.3-2.4 (6H,m), 2.18(3H,s), 3.48 (2H,ABq,J=18 Hz), 3.63 (2H,s), 4.73 (1H,t), 4.92 (2H,ABq,J=12 Hz), 5.04 (1H,d,J=5 Hz), 5.65 (1H,dd,J=5 and 8 Hz), 7.89 (4H,s), 8.77 (1H,d,J=8 Hz) ppm IR(KBr): 1775, 1740, 1715, 1640, 1530 cm$^{-1}$

EXAMPLE 6

To a solution of 0.59 g of 7β-[2-(2-chloroacetamidothiazol-4-yl)-(Z)-2-methoxyiminoacetamido]-3-hydroxymethyl-3-cephem-4-carboxylic acid triethylamine salt and 10 mg of 4-(dimethylamino)pyridine in 10 ml of methylene chloride was added 92 mg of diketene at 0° C., and the mixture was stirred at that temperature for 15 minutes. After completion of the reaction, the reaction mixture was poured into 10 ml of cold water, thereto was added 5 ml of tetrahydrofuran, and the solution was adjusted to pH 2.0 by addition of 1N hydrochloric acid. The organic layer was taken, and the aqueous layer was extracted with 7.5 ml of a methylene chloride-tetrahydrofuran mixture (2:1 by volume). The organic layers were combined and concentrated to dryness. The residue was dissolved in aqueous acetonitrile (acetonitrile 20 ml-water 20 ml), adjusted to pH 6.5 by addition of 1N sodium hydroxide aqueous solution, concentrated and lyophilized to give 0.57 g of 7β-[2-(2-chloroacetamidothiazol-4-yl)-(Z)-2-methoxyiminoacetamido]-3-(3-oxobutyryloxymethyl)-3-cephem-4-carboxylic acid sodium salt. Yield 95.6%

NMR(DMSO-d$_6$): δ 2.18 (3H,s), 3.19 and 3.70 (2H,ABq,J=17 Hz), 3.59 (2H,s), 3.89 (3H,s), 4.36 (2H,s), 4.85 and 5.08 (2H,ABq,J=12 Hz), 5.01 (1H,d,J=5 Hz), 5.63 (1H,dd,J=5×8 Hz), 7.41 (1H,s), 9.56 (1H,d,J=8 Hz) ppm IR(KBr): 1768, 1680, 1608 cm$^{-1}$

REFERENCE EXAMPLE 1 [Case where 4-(dimethylamino)pyridine was not used]

To a solution of 1.56 g of 7β-(D-5-carboxy-5-phenoxycarbonylaminovaleramido)-3-hydroxymethyl-3-cephem-4-carboxylic acid ditriethylamine salt in 13 ml of methylene chloride was added 0.23 g of diketene at 0° C., and the mixture stirred at that temperature for 15 minutes. Water (12.5 ml) was added to the reaction mixture, the methylene chloride distilled off under reduced pressure, and the remaining aqueous solution assayed by high-performance liquid chromatography. It was found that 0.014 g of 7β-(D-5-carboxy-5-phenoxycarbonylaminovaleramido)-3-(3-oxobutyryloxymethyl)-3-cephem-4-carboxylic acid disodium salt was contained in said aqueous solution. Yield 1.0%.

REFERENCE EXAMPLE 2

The procedure of Reference Example 1 was followed in the same manner except that the reaction temperature was maintained at 40° C. The yield of 7β-(D-5-carboxy-5-phenoxycarbonylaminovaleramido)-3-(3-oxobutyryloxymethyl)-3-cephem-4-carboxylic acid disodium salt was 0.454 g, or 32.6%.

While, as is evident from the data obtained above in Reference Examples 1 and 2, the prior art method (described in U.K. Patent No. 1 544 103) of producing the 3-butyryl compounds, which does not use such 4-(tertiary-amino)pyridine as 4-(dimethylamino)pyridine in reacting the 3-hydroxy compounds with diketene, can allow the reaction to progress only to an unsatisfactory extent, giving the desired products in very low yields (not more than 32.6%), when the reaction is carried out at a low temperature (0° C.) or a higher temperature (40° C.) for a short period of time (15 minutes), the method according to the invention can allow the reaction to progress to completion even at a low temperature (0° C.) in a short period of time (15 minutes), giving the desired products in high yields (not less than 90%), as is seen in Examples 1 and 2. The above-mentioned reference examples and working examples have thus established that the method according to the invention requires a much shorter reaction period as compared with the prior art.

What we claim is:

1. In a method of producing a 3-(3-oxobutyryloxymethyl)-3-cephem-4-carboxylic acid by the reaction of a 3-hydroxymethyl-3-cephem-4-carboxylic acid with a diketene, the improvement which comprises conducting said reaction in the presence of a catalytically effective amount of a 4-(tertiary-amino)pyridine, whereby the reaction of said 3-hydroxymethyl-3-cephem-4-carboxylic acid with said diketene is facilitated in a relatively short period of time to form said 3-(3-oxobutyryloxymethyl)-3-cephem-4-carboxylic acid.

2. A method of producing a 3-(3-oxobutyryloxymethyl)-3-cephem-4-carboxylic acid in accordance with claim 1, wherein the facilitation of said reaction includes the substantial completion thereof within twenty minutes.

3. A method of producing an 7-amino-3-(3-oxobutyryloxymethyl)-3-cephem-4-carboxylic acid which comprises reacting an 7-acylamino-3-hydroxymethyl-3-cephem-4-carboxylic acid with diketene in the presence of a catalytically effective amount of a 4-(tertiary-amino)pyridine and subjecting the resulting 7-acylamino-3-(3-oxobutyryloxymethyl)-3-cephem-4-carboxylic acid to deacylation at the 7-position thereof.

4. A method according to claim 1, wherein the 3-(3-oxobutyryloxymethyl)-3-cephem-4-carboxylic acid is a 3-cephem compound having an 3-oxobutyryloxymethyl group at position 3 and a carboxyl group at position 4, or a salt or ester thereof, and the 3-hydroxymethyl-3-cephem-4-carboxylic acid is a 3-cephem compound having a hydroxymethyl group at position 3 and a carboxyl group at position 4, or a salt or ester thereof.

5. A method according to claim 3, wherein the 7-amino-3-(3-oxobutyryloxymethyl)-3-cephem-4-carboxylic acid is a 3-cephem compound having an amino group at position 7, an 3-oxobutyryloxymethyl group at position 3 and a carboxyl group at position 4, or a salt or ester thereof, the 7-acylamino-3-hydroxymethyl-3-cephem-4-carboxylic acid is a 3-cephem compound having an acylamino group at position 7, a hydroxymethyl group at position 3 and a carboxyl group at position 4, or a salt or ester thereof and the 7-acylamino-3-(3-oxobutyryloxymethyl)-3-cephem-4-carboxylic acid is a 3-cephem compound having an acylamino group at position 7, an 3-oxobutyryloxymethyl group at position 3 and a carboxyl group at position 4, or a salt or ester thereof.

6. A method of producing a compound of the formula:

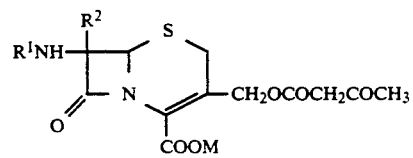

wherein $R^1$ is a hydrogen atom, a protective group or an acyl group, $R^2$ is a hydrogen atom or a methoxy or formylamino group and M is a hydrogen atom, a salt-forming group or an ester residue, which comprises reacting a compound of the formula:

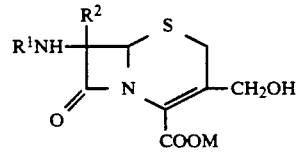

wherein the symbols are as defined above with diketene in the presence of a catalytically effective amount of a 4-(tertiary-amino)pyridine.

7. A method of producing a compound of the formula:

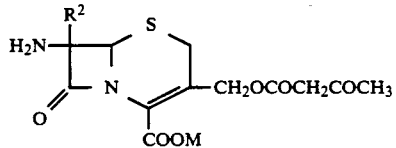

wherein $R^2$ is a hydrogen atom or a methoxy or formylamino group and M is a hydrogen atom, a salt-forming group or an ester residue, which comprises reacting a compound of the formula:

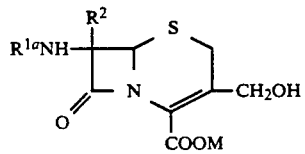

wherein $R^{1a}$ is an acyl group and the other symbols are as defined above with diketene in the presence of a catalytically effective amount of a 4-(tertiary-amino)-pyridine and subjecting the resulting compound of the formula:

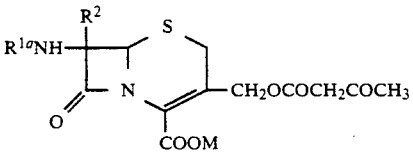

wherein the symbols are as defined above to deacylation at the 7-position thereof.

8. A method of producing a compound of the formula:

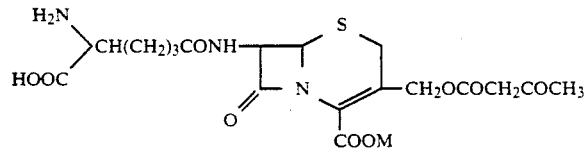

wherein M is a hydrogen atom, a salt-forming group or an ester residue, and the amino and/or carboxyl group may be protected, which comprises reacting a compound of the formula:

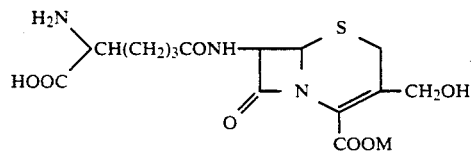

wherein M is as defined above and the amino and/or carboxyl group may be protected with diketene in the presence of a catalytically effective amount of a 4-(tertiary-amino)pyridine.

9. A method of producing a compound of the formula:

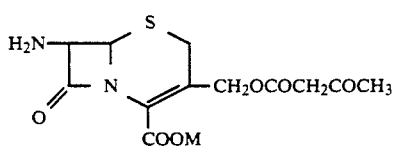

wherein M is a hydrogen atom, a salt-forming group or an ester residue, which comprises reacting a compound of the formula:

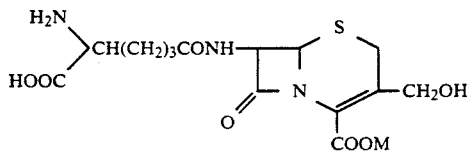

wherein M is as defined above and the amino and/or carboxyl group may be protected with diketene in the presence of a catalytically effective amount of a 4-(tertiary-amino)pyridine and subjecting the resulting compound of the formula:

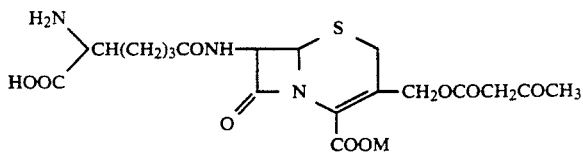

wherein M is as defined above and the amino and/or carboxyl group may be protected to deacylation at the 7-position thereof.

10. A method according to claim 1, wherein the 4-(tertiary-amino)pyridine is a compound of the formula:

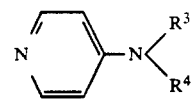

wherein $R^3$ and $R^4$ are the same or different and each is an alkyl group, or $R^3$ and $R^4$, together with the adjacent nitrogen atom, represent a cyclic amino group.

11. A method according to claim 1, wherein the reaction is conducted at a temperature within a range of $-40°$ to $40°$ C.

12. A method according to claim 10, wherein the 4-(tertiary-amino)pyridine is selected from the group consisting of 4-(dimethylamino)pyridine, 4-(diethylamino)pyridine, 4-(di-n-propylamino)pyridine, 4-(diisopropylamino)pyridine, 4-(N-methyl-N-ethylamino)pyridine, 4-(N-ethyl-N-propylamino)pyridine, 4-pyrrolidinopyridine, 4-(4-methylpyrrolidino)pyridine and 4-piperidinopyridine.

13. A method according to claim 3, wherein the 4-(tertiary-amino)pyridine is a compound of the formula:

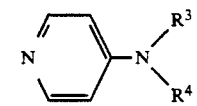

wherein $R^3$ and $R^4$ are the same or different and each is an alkyl group, or $R^3$ and $R^4$, together with the adjacent nitrogen atom, represent a cyclic amino group.

14. A method according to claim 6, wherein the 4-(tertiary-amino)pyridine is a compound of the formula:

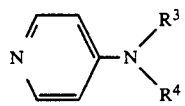

wherein R³ and R⁴ are the same or different and each is an alkyl group, or R³ and R⁴, together with the adjacent nitrogen atom, represent a cyclic amino group.

15. A method according to claim 14, wherein the 4-(tertiary-amino)pyridine is selected from the group consisting of 4-(dimethylamino)pyridine, 4-(diethylamino)pyridine, 4-(di-n-propylamino)pyridine, 4-(diisopropylamino)pyridine, 4-(N-methyl-N-ethylamino)pyridine, 4-(N-ethyl-N-propylamino)pyridine, 4-pyrrolidinopyridine, 4-(4-methylpyrrolidino)pyridine and 4-piperidinopyridine.

16. A method according to claim 7, wherein the 4-(tertiary-amino)pyridine is a compound of the formula:

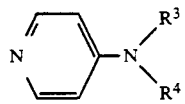

wherein R³ and R⁴ are the same or different and each is an alkyl group, or R³ and R⁴, together with the adjacent nitrogen atom, represent a cyclic amino group.

17. A method according to claim 8, wherein the 4-(tertiary-amino)pyridine is a compound of the formula:

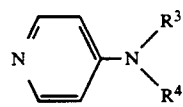

wherein R³ and R⁴ are the same or different and each is an alkyl group, or R³ and R⁴, together with the adjacent nitrogen atom, represent a cyclic amino group.

18. A method according to claim 9, wherein the 4-(tertiary-amino)pyridine is a compound of the formula:

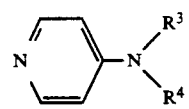

wherein R³ and R⁴ are the same or different and each is an alkyl group, or R³ and R⁴, together with the adjacent nitrogen atom, represent a cyclic amino group.

19. A method according to claim 6, wherein the 4-(tertiary-amino)pyridine is present in an amount of 0.001 to 1 mole per mole of diketene.

20. A method according to claim 1, wherein the 4-tertiary-amino)pyridine is present in an amount of 0.001 to 1 mole per mole of diketene.

* * * * *